(12) United States Patent
Dörge et al.

(10) Patent No.: US 10,550,359 B2
(45) Date of Patent: Feb. 4, 2020

(54) CONTAINER FOR CULTURING, MICRO MANIPULATION AND IDENTIFICATION OF SMALL SPECIMENS

(71) Applicant: HertART ApS, Greve (DK)

(72) Inventors: Henrik Carlheim Dörge, Gadstrup (DK); Bjarne Bo Jensen, Viby Sjælland (DK)

(73) Assignee: HERTART APS, Greve (DK)

( * ) Notice: Subject to any disclaimer, the term of this patent is extended or adjusted under 35 U.S.C. 154(b) by 663 days.

(21) Appl. No.: 14/939,941

(22) Filed: Nov. 12, 2015

(65) Prior Publication Data

US 2016/0097026 A1    Apr. 7, 2016

Related U.S. Application Data

(63) Continuation of application No. 13/878,487, filed as application No. PCT/DK2011/050401 on Oct. 21, 2011, now abandoned.

(30) Foreign Application Priority Data

Oct. 22, 2010   (DK) ................................ 2010 70447

(51) Int. Cl.
*C12M 1/00* (2006.01)
*C12M 3/00* (2006.01)
(Continued)

(52) U.S. Cl.
CPC ............ *C12M 21/06* (2013.01); *C12M 21/00* (2013.01); *C12M 23/12* (2013.01); *C12M 23/38* (2013.01);
(Continued)

(58) Field of Classification Search
CPC ...... C12M 21/00; C12M 21/06; C12M 23/12; C12M 23/38; C12M 25/06; B01L 3/508;
(Continued)

(56) References Cited

U.S. PATENT DOCUMENTS 4,945,061 A * 7/1990 Iskander ................ C12M 23/10
                                                                        435/305.1
4,986,965 A    1/1991 Ushikubo
(Continued)

FOREIGN PATENT DOCUMENTS

EP    0 627 358 A1    12/1994
EP    0 866 122 A2    9/1998
(Continued)

OTHER PUBLICATIONS

Tachibana et al., English-language machine translation of Japanese document JP2006-280298A. Retrieved on Sep. 18, 2017. (Year: 2006).*

(Continued)

*Primary Examiner* — Liban M Hassan
(74) *Attorney, Agent, or Firm* — Knobbe Martens Olson & Bear LLP

(57) ABSTRACT

A disposable polymer container for manipulation of small specimens adapted to optimize heat transfer between an external heating element and specimens herein contained. In particular, this invention relates to the field of containers for Assisted Reproductive Technology hereunder In-vitro fertilization (IVF).

19 Claims, 7 Drawing Sheets

Related U.S. Application Data

(60) Provisional application No. 61/405,956, filed on Oct. 22, 2010.

(51) Int. Cl.
*C12M 1/32* (2006.01)
*C12M 1/12* (2006.01)

(52) U.S. Cl.
CPC ......... *C12M 25/06* (2013.01); *C12N 2533/30* (2013.01)

(58) Field of Classification Search
CPC ........... B01L 3/50851; B01L 2200/028; B01L 2300/022; B01L 2300/0851; B01L 2300/0858
USPC .................................. 435/289.1, 325, 305.4
See application file for complete search history.

(56) References Cited

U.S. PATENT DOCUMENTS

| | | |
|---|---|---|
| 5,447,234 A | 9/1995 | Faulstick et al. |
| 5,447,237 A | 9/1995 | Carter et al. |
| 5,691,194 A | 11/1997 | Gordon |
| 5,766,937 A | 6/1998 | Lahm et al. |
| 7,008,788 B2 | 3/2006 | Schremp et al. |
| 2004/0161855 A1 | 8/2004 | Kvasnik et al. |
| 2008/0064090 A1 | 3/2008 | Whittlinger |
| 2008/0090287 A1 | 4/2008 | Larsen |

FOREIGN PATENT DOCUMENTS

| | | |
|---|---|---|
| JP | 2001-201505 | 7/2001 |
| JP | 2006-2800298 A | 10/2006 |

OTHER PUBLICATIONS

International Search Report for PCT/DK2011/050401 dated Feb. 22, 2012.

\* cited by examiner

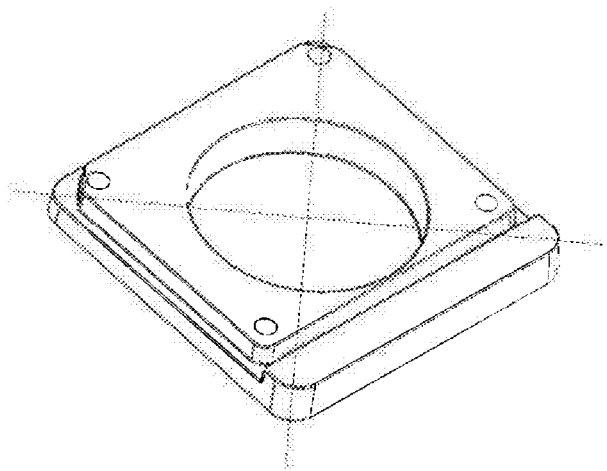
FIG. 8
FIG. 9a
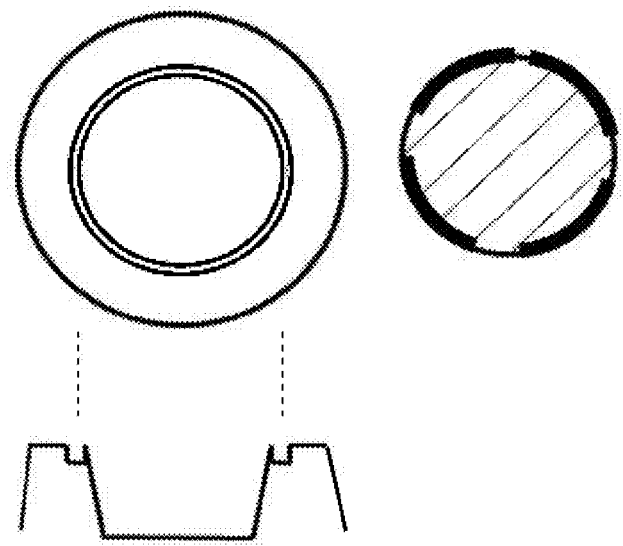
FIG. 9b
FIG. 9c

CONTAINER FOR CULTURING, MICRO MANIPULATION AND IDENTIFICATION OF SMALL SPECIMENS

CROSS-REFERENCE TO RELATED APPLICATIONS

This application is a continuation of U.S. patent application Ser. No. 13/878,487, filed on Jun. 20, 2013, which claims the benefit and priority to and is a U.S. National Phase Application of PCT International Application No. PCT/DK2011/050401, filed on Oct. 21, 2011, designating the United States of America and published in the English language, which is an International Application of and claims the benefit of priority to Danish Patent Application No. PA 2010 70447, filed on Oct. 22, 2010, and U.S. Provisional Application No. 61/405,956, filed on Oct. 22, 2010. The disclosures of the above-referenced applications are hereby expressly incorporated by reference in their entireties.

BACKGROUND OF THE INVENTION

Field of the Invention

This invention relates to the field of containers for culturing and manipulating small specimens.

In particular, this invention relates to the field of containers for Assisted Reproductive Technology hereunder In-vitro fertilization (IVF).

Description of the Related Art

Disposable sterile polymer containers such dishes and well plates are useful when manipulating smaller specimens in liquid media, e.g during artificial reproductive technologies such as In-Vitro Fertilisation (IVF) by the micro manipulation and culturing of spermatozoa, oocytes and embryos.

Current containers used for micro manipulation within IVF are mostly generic, off-the-shelf, dishes developed for standard tissue culture. The micro manipulation of immature oocytes, mature oocytes, gametes, zygotes, embryos, cleavage stage embryos, blastocyst stage embryos, precursor cells, and such, referred to herein as "specimens", are done in standard 35 mm, 50 mm or 60 mm Petri Dish or 4 Well Dish, containers with few unique features, each dish or well simply has flat transparent bottoms and substantially vertical side walls.

Flat and transparent bottom is important for most applications as it facilitates the microscopy of the biological material within the dish or well. One additional feature of these generic dishes and well plates is the elevation of the flat bottom surface from the working table by a rim. This rim being at the circumference below the bottom surface and has generally the advantage of reinforcing the strength of the dish or well plate to reduce internal stresses and avoid distortion of the flat bottom during solidification of the polymer article during production.

Further the rim elevates the bottom to avoid scratching of the bottom surface during stacking of the dish or well plate for packaging, transportation and during incubation. Scratching reduces visibility of the specimens during use and during microscopy.

Within the field of IVF, the human oocytes and embryos must be held as closely as possible at a stable 37 degrees Celsius. The ability to control the temperature of the bottom of the dish and so also the temperature of the embryos and oocytes has proven to be critical for successful fertilization, for example the spindles of the oocytes might disassemble within minutes during temperature change.

The wall structure utilized on commercially available well plates has lower wall base level than the level of the bottom, not allowing the contact between bottom surface and heated working surface below.

Within IVF the rim elevating the bottom of generic dishes and plates are a disadvantage since it introduces an air gap between the surface of the heated working table and the bottom of the dish or well. As air is not a good heat transporter, the temperature at the elevated bottom of the dishes and wells can be hard to control on heated working surfaces. Often the oocyte/embryo manipulations are done within a laminar air flow hood. The laminar air flow creates air movements which makes the control of the temperature more difficult.

However removing the rim below the polymer specimen container such as on a commercially available Petri dish, reduces the structural integrity of the polymer container and increases the likelihood of distortion of the bottom surface during solidification of the polymer container during production, as well as increasing the risk of scratching the surface during stacking for packaging, transportation and incubation.

Another problem is related to traceability of specimens from patients/donors in the various standard containers used during IVF procedure, is the fact that traditional dishes are of a Petri dish type or well plate type, where the container is fully covered by a lid. Identification can be made on the lid, however this lid can potentially fit other dishes of similar type potentially leading to mismatch of specimens and patients/donors.

It would be highly desirable to provide a specimen container allowing the flat bottom to be in contact with the heated working table, while allowing the stacking of the container without scratching the bottom surface.

It would further be desirable that the container had structure comprising area for identification means not being on the detachable lid.

OBJECT OF THE INVENTION

It is an object of this invention to provide a polymer specimen container having improved temperature transfer, i.e. an improved ability of transferring heat from heated working surface. As temperature transfer is meant the ability of transferring heat, i.e. keeping the temperature in the polymer specimen as close as possible to the temperature of the heated working surface.

It is further an object of this invention to provide a lid structure allowing stacking of the containers with lid without scratching the bottom surface.

It is a further object of this invention to provide improved means for identification of specimens.

It is a further object of the present invention to provide an alternative to the prior art.

These and other objects are achieved by the aspect and embodiments of the invention described and shown herein.

SUMMARY OF THE INVENTION

Thus, the above described object and several other objects are intended to be obtained in a first aspect of the invention by providing a polymer specimen container comprising: a specimen carrier, said carrier comprising a bottom base externally flat connected to a wall, said wall comprising an open hollow structure adapted to avoid twisting of said bottom base during the polymer specimen container production process.

The main effect of said structure is to secure contact between flat bottom base and working table below.

In some embodiments said open wall structure may have its lowest level above the lowest level of the bottom base.

The invention is particularly, but not exclusively, advantageous to provide a polymer specimen container having improved temperature transfer from heated working surface through the bottom of the container to the specimens by securing full contact between the downwardly flat bottom of the container and the heated working surface, utilizing an open wall construction with ridges and recesses for stabilizing against distortion of the flat bottom surface of the container as well as utilizing a wall base being above the level of the bottom base.

By providing adapted means for contacting the ridges and recesses of the open wall construction, the invention has also the advantage of allowing stacking of the containers with lid without scratching the bottom surface ensuring full visibility of the specimens through the transparent bottom surface during use.

The invention is particularly, but not exclusively, advantageous to provide improved means for identification of specimens by providing area for identification on the open wall construction, which is not covered by the lid.

This invention relates to an improved specimen container for the handling, micro manipulation, micro injection and/or biopsy of spermatozoa, sperm precursor cells, oocytes, preimplantation embryos, zygotes, blastocysts, embryonic cells and stem cells, collectively referred to hereinafter as "specimen" or "specimens".

The specimens must be held as closely as possible at a stable 37 degrees Celsius, especially during critical procedures such as IVF, making use of heated working surface below the specimen container often placed with a laminar airflow hood. As air, and especially moving air, is not an optimal heat conductor, close contact between the bottom of the specimen container and the heated working table is desirable.

The high degree of flatness of the bottom base is achieved during the solidification of the polymer material of the polymer specimen container during its production.

The open hollow wall structure secures stability to the specimen carrier preventing twisting or distortion of the bottom base, thereby facilitating the formation of a bottom base with a high degree of flatness with no need for structural reinforcement structures below the bottom base.

Flat is herein defined as substantial parallel to the surface on which the container is placed, e.g. zero degree of inclination in respect to the surface on which the container is placed.

In some embodiment the open hollow structure comprises recesses and ridges adapted to provide stable support to specimen carrier, thereby avoiding twisting of said bottom base during said polymer specimen container production process.

In some embodiment the open wall structure has its lowest level above the lowest level of said bottom base externally flat. This allows for a completely flat surface of the external bottom base.

In another embodiment the polymer specimen container further comprises a lid, said lid comprising a top and a bottom surface, wherein said top surface comprises protrusions complementary to at least one of the recesses in said open hollow wall structure, thereby avoiding scratching of the bottom surface during stacking.

Complementary is herein defined as to be able to be combined so that the protrusions in the top surfaces of the lid matches the recesses on the open wall structure so that the protrusions can be contained into the recesses allowing for stacking of the polymer specimens containers avoiding risk of contact to the bottom base of the containers, and thereby avoiding scratching of the bottom surface.

In another embodiment the open hollow structure comprises identification means.

The identification means may so be placed on, above or below the open hollow structure of the wall or in combinations hereof.

Examples of identification means may be for examples barcode, inscription, embossed text, writing or RFID-tags. The wall base level above level of the bottom base allows barcodes or other identification means to be placed on the container and bend around the wall base without interfering with the temperature transfer to the flat bottom base remaining in contact with the working surface. Identification means may so be placed in different areas on, above or below the open hollow structure of the wall or combinations hereof.

The bottom base externally flat is characterized by an internal surface, where the specimen is carried and contained and an external surface in contact with the external environment.

In some embodiments at least part of the internal surface of said bottom base is treated so as to modify its surface properties. For example said internal surface of said bottom base externally flat may be functionalized by surface modification.

In another embodiment the invention has a circular or substantially square outer geometry making microscopy easy using conventional rotation of the container or making use of more modern XY stage stations.

In another embodiment the invention has a circular innermost wall structure situated in the center of the container structure ensuring centrically rotations of the well if the dish is to be rotated for microscopy purposes.

In another embodiment the bottom base externally flat comprises one or more individually separated wells. These wells, when the polymer specimen container is in use holds liquid medium sustaining the specimens. The individually separated wells allows the wells to be homogeneously temperate as well as ensure no cross-contamination from one well to another. If drop culture is used a potentially collapsing drop will not interfere with other drops within the same container.

In another embodiment the internal surface of the bottom base of said individually separated wells has an inclination. This inclination, from few degrees up to 45°, allows specimens to settle not contacting the wall of the well. This in turn allows easy manipulation of the specimen.

This solves the problem of small specimens e.g. embryos hiding at the corner between the wall and the bottom of the well. The slope allows the specimen to gradually be transported by gravity towards the bottom where it can easily be located by microscopy and easily accessed by manipulating tools.

In another embodiment of the invention at least the bottom of the wells is functionalized by surface modification.

The container can be used for a wide range of specimens of human and animal cells, embryos, embryonic cells, oocytes, spermatozoa, sperm precursor cells, blastocysts and stem cells with all such specimens receiving the same benefits In a particular embodiment of the invention the intended use is for Artificial Reproductive Technology, In a second aspect the invention provides a method for producing a polymer specimen container wherein the presence of an open hollow structure comprising recesses and ridges prevents distortion of said flat bottom base during said polymer specimen carrier solidification.

The first and other aspect of the present invention may each be combined with any of the other aspects and embodiments.

Other aspects, advantages and novel features of the invention will become more apparent from the following detailed description of the invention when considered in conjunction with the accompanying drawings.

BRIEF DESCRIPTION OF THE DRAWINGS

The polymer specimen container according to the invention will now be described in more detail with regard to the accompanying figures. The figures show one way of implementing the present invention and is not to be construed as being limiting to other possible embodiments falling within the scope of the attached claim set.

FIG. 8 shows a top view on an exemplary container having a fifth appearance with a centred well in accordance with embodiments of the invention.

FIG. 9a shows a top view and FIG. 9b the corresponding lid and FIG. 9c the cross-sectional view of an exemplary container having a sixth appearance in accordance with some aspect of the invention.

DETAILED DESCRIPTION OF THE PREFERRED EMBODIMENT

Figure 1C:
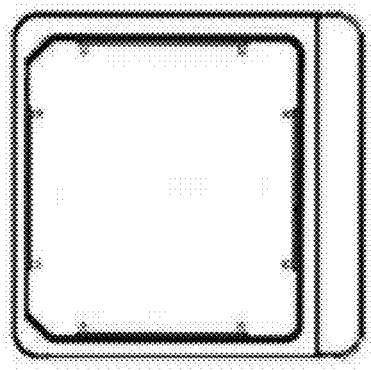
FIG. 1a shows a top view of an exemplary container and FIG. 1b is the corresponding lid and FIG. 1c is the container with lid not covering the identification area in accordance with embodiments of the invention.

With reference to the drawings for purpose of illustration, the present invention is embodied in a dish (FIG. 1a) with a separate lid (FIG. 1b) not covering the dedicated identification area (FIG. 1c) securing constant visibility during use.

Figure 2A:
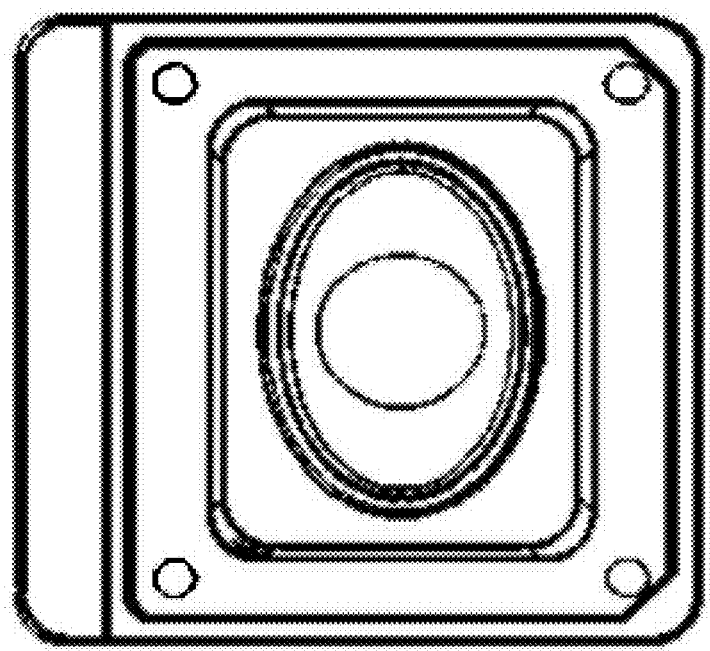
FIG. 2a shows a top view and FIG. 2b shows a cross-sectional view of an exemplary container having a secondary appearance with an innermost wall and an outer most wall and an area for identification here between in accordance with embodiments of the invention.
Figure 2B:
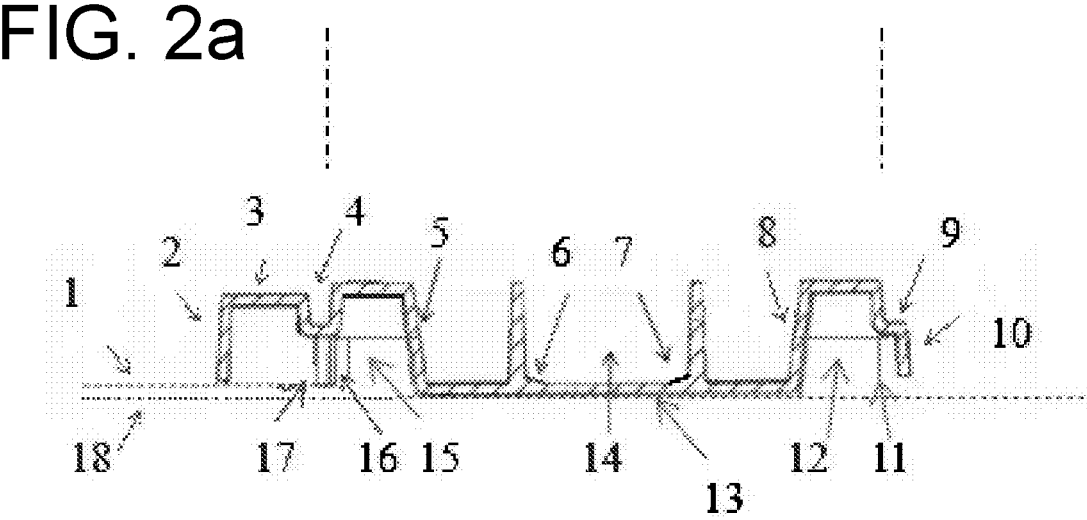
Figure 3:
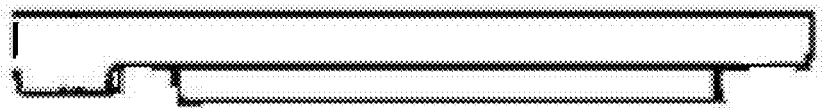
FIG. 3 shows a side view of an exemplary container without lid having a bottom surface being downwardly flat and having a wall base level higher than the bottom base level in accordance with embodiments of this invention.

On FIG. 2 the lid fits into structures (4,9). A writing area (3) is positioned between the innermost wall (5) and the outermost wall (2) being part of the open wall structure on one side of the bottom surface, just like the innermost wall (8) and the outermost wall (10) also being part of the open wall structure. The open wall structure has reinforcements by ridges and recesses (11,12,15,16). The reinforced open wall structure prevents distortion of the polymer container during polymer solidification. The open wall structure is interconnected to a bottom base (13) having a surface being downwardly flat. The bottom base (13) has a base level (18) lower than the lowest level (1) of any other structures on the article securing full contact of the bottom surface to the underlying often heated working surface and thereby securing optimal temperature transfer to the specimens to be contained inside the container e.g. in a well (14). The well could be separated by a wall structure having a slope (6,7) between the actual wall structure and the bottom structure, securing positioning of the specimen away from the wall structure of the well. If a label, barcode or RFID tag is to be placed below the container for imaging purpose it may be placed on the outermost wall structure (2) and bend underneath the slightly elevated wall structure and be supported by a protrusion (17).

Figure 4:
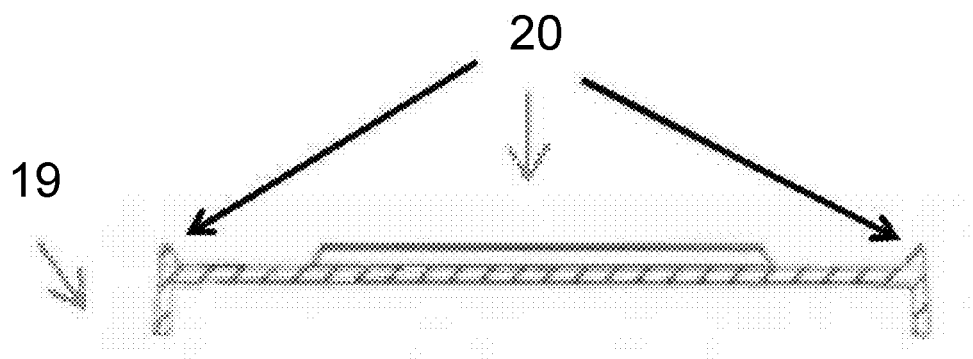
FIG. 4 shows a cross-sectional view of the lid having protrusions in accordance with embodiments of the invention.
Figure 5:
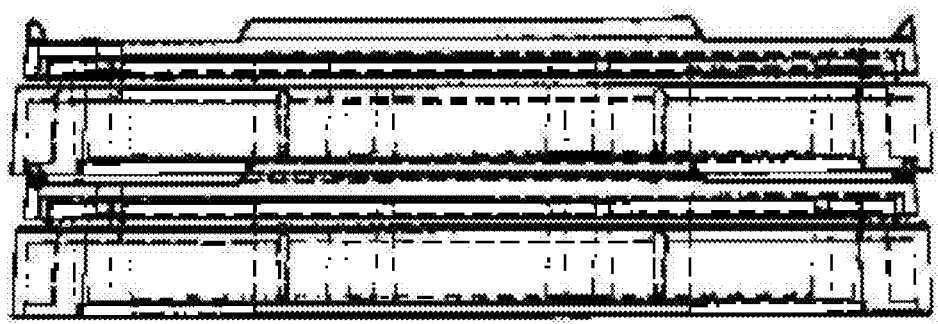
FIG. 5 shows a back-side view of to exemplary containers with lid stacked on top of each other. The lid having protrusions in accordance with embodiments of the invention making contact with recesses on the open wall structure allowing stacking of containers or carriers without scratching the bottom surface.
Figure 6:
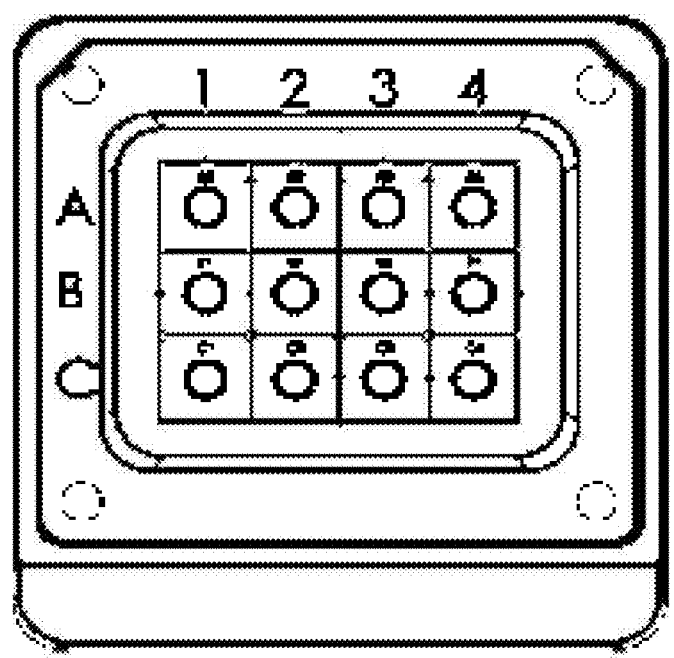
FIG. 6 shows a top view of an exemplary container having a third appearance with separated wells in accordance with embodiments of the invention.
Figure 7:
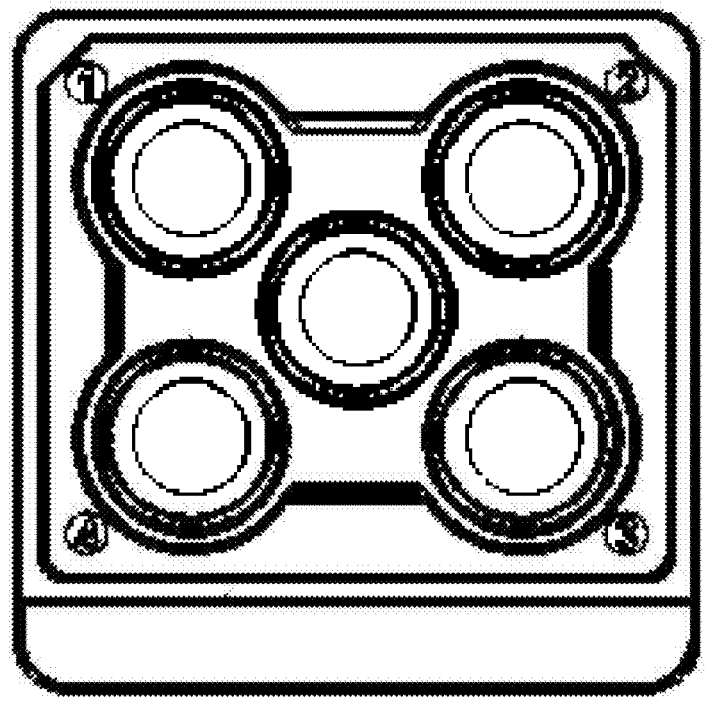
FIG. 7 shows a top view of an exemplary container having a forth appearance with a slope in each separated well in accordance with embodiments of the invention.

The lid in FIG. 4 has a rim (19) to secure stability when positioned on the container. The lid also has a protrusion (20) which makes contact on ridges and recesses on the open wall structure of an adjacent container during stacking, making sure the bottom of the container is not scratched during stacking as well as to facilitate easy grasping. Stacking is illustrated on FIG. 5.

Figure 1B:
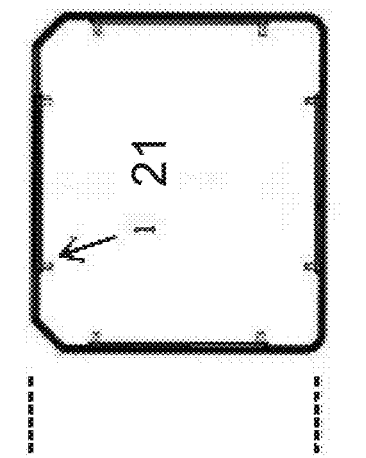
Figure 1A:
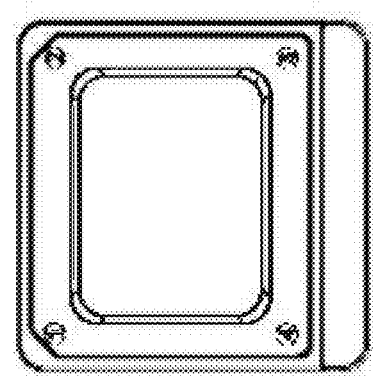

The lid, FIG. 1b, may further have small protrusions (21) securing gas exchange between the outside of the container and the inside of the container during use.

Definitions

Sterile means free from living bacteria and other microorganisms. Sterilisation is the process by which living organisms are removed or killed to the extent that they are no longer detectable in standard cell culture media in which they had previously proliferated. Sterility Assurance Level of six-log reduction (also termed log of minus 6 reduction or ten to the minus six reductions) is considered acceptable for many medical devices.

Open wall structure means a wall structure consisting of a non-closed wall structure persisting in more than one plane.

Innermost wall structure means the wall nearest to the inside of the container or carrier.

Outermost wall structure means the wall nearest to the outside of the container or carrier.

Downwardly flat bottom base and externally flat bottom base means that the bottom area facing downwards, towards the outside of the container, is flat. The part of the bottom area facing upwards, towards the inside of the container could be flat, but could also contain well structures.

Square with or without rounded corners means a substantially square geometry with corner angle of 90 degrees or rounded.

Center of the dish means the center of the dish confined by the outermost wall.

Individually separated wells means wells separated by a wall structure or embedded in the bottom structure in a way so liquid in one well is separated from liquid in another well.

Slope means a ramp with an inclination between 0 and 90 degrees. A slope in the bottom of a well may interconnect the bottom area with the wall structure of the well.

Functionalized by surface modification means modifying the surface properties e.g. by use of electric discharge, plasma, biological molecules, irradiation, structuring, material embedding, chemical or molecular vapor deposition or other means.

Identification marking means marking with text, print, labels, inscription, transmitter or other means in order trace container and content RFID means Radio-frequency Identification. RFID is a technology that incorporates the use of electromagnetic spectrum to uniquely identify an object.

Assisted Reproductive Technology (ART) is a general term referring to methods used to achieve Pregnancy by artificial or partially artificial means. It is a reproductive technology used primarily in Infertility treatments, such as InVitro Fertilisation.

In Vitro Fertilization (IVF) is a laboratory procedure in which sperm are placed with an unfertilized egg in a dish to achieve fertilization.

XY-stage station means automated or manual positioning table delivering smooth and accurate two-dimensional motion.

Collapsing drops means liquid drops placed on a solid support, e.g. bottom surface of a polymer container, and not having a measurable contact angle with the solid support, a phenomenon occurring when liquid is placed on hydrophilic surfaces and a well defined drop with measurable contact angle cannot be maintained.

Protrusion means something that bulges out or is protuberant and thereby raises above the surrounding support.

Meiose activation means activating cell division necessary for sexual reproduction Chemical vapor deposition (CVD) means a chemical process used to produce high-purity, high-performance solid materials. The process is generally used in the semiconductor industry to produce thin films. In a typical CVD process, the substrate is exposed to one or more volatile precursors which react and precipitate or decompose on the substrate surface to produce the desired deposit Molecular vapor deposition (MVD) means an enhancement of the conventional vapor deposition of ultra-thin layers. It is a non-plasma vacuum process where volatile components in gas phase react to form a solid deposit and gaseous by-products. In MVD the reagents concentrations control the deposition rate. Reagents are distributed uniformly in the system by means of pressure and MVD is performed as a batch process so that no new reagent is added to the process during the deposition. MVD is not an invasive technique, the low temperature, the absence of plasma and the introduction of reagents as gases do not damage the substrate.

Base height means the height of the supporting base of any structure on the article.

Bottom base means the lowest base of the bottom surface.

Wall base means the lowest surface of the open wall structure. When the wall is at one end connected to the bottom surface and stretching only onto one side of the bottom surface, the wall base is defined as being above the level of the bottom base.

Flat is herein defined as substantial parallel to the surface on which the container is placed, e.g. zero degree of inclination in respect to the surface on which the container is placed.

Working surface is defined as the surface onto which the container or carrier in placed during use. E.g. this working surface may be a heated or non-heated surface, a structured surface within an incubator, a surface within a laminar airflow hood, the surface of the lid of another container or carrier and more.

EXAMPLES

Polymer specimen container with open wall structure, flat bottom base in contact with working surface, area for identification, and optionally slope between wall structure of the well and bottom of the well The polymer container of the present invention may have any suitable size for the intended use.

In particular polymer container being substantially square or square with rounded corners having a side length of 25 mm or less, such as 20 mm or less, 15 mm or less, 10 mm or less such as approximately 7.5 mm. A substantially square geometry is useful during microscopy using an XY stage moving the container in X- and Y directions.

In particular polymer container being substantially circular having a diameter of 120 mm or less, such as 90 mm or less, such as 60 mm or less, such as 50 mm or less, such as 40 mm or less. A substantially circular geometry is useful during microscopy rotating the container by hand.

In particular polymer container being substantially square or square with rounded corners containing circular well(s) having any suitable size for the intended use, in particular well diameter of 90 mm or less, 60 mm or less, 45 mm or less, 35 mm or less, 10 mm or less, 5 mm or less. A substantially square or square dish with rounded corners containing a circular well with center at the center of the container is useful during microscopy rotating the container by hand. Centered or a non-centered well is useful for micro drop culture as well as collection and transferring specimens. Several wells within the same container are useful for culturing embryos separately and securing no cross contamination between embryo cultures, also in the event of collapsing drops.

The well(s) may have any shape suitable for intended use. When used during procedures where tools are applied from left and right hand side at the specimens within the well, a circular, oval or rectangular well shape may be preferred. When used during embryo culture a circular well may be preferred. The individual wells may optionally have a slope between the flat bottom of the well and the well structure, useful for preventing small specimens to hide in the otherwise sharp angles. The slope ensures that the small specimens such as embryos are transferred to the bottom of the well by gravity and easily accessible at a known distance from the wall of the well. The slope of the present invention may have suitable size for intended use, in particular slope angle of 89 degrees or less, 45 degrees or less, 30 degrees or less, such as 25 degrees.

Some procedures require larger amounts of media within the container, some requires smaller amount of media, and some requires easy access with tools approaching the containers from the sides. The height of the container may have any shape suitable for intended use, in particular 20 mm or less, 15 mm or less, 10 mm or less, 9 mm or less, 8 mm or less, 7 mm or less, 6 mm or less, 5 mm or less.

In contrast to a traditional Petri dish the invention provides an open wall structure One benefit being that part of the area on the open wall structure provides an identification area suitable for marking, engraving, labeling, barcode, RFID tag or the like. The Identification area of the present invention may have suitable size for the intended use. In particular area of 100 $cm^2$ or less, 50 $cm^2$ or less, 25 $cm^2$ or less, 10 $cm^2$ or less, 8 $cm^2$ or less.

Another benefit being that the open wall structure interconnected by a bottom structure being downwardly flat and said bottom base having a lower base level than the base of the wall structure is that the bottom surface is being in close contact with the external working surface below, which may be a heated table. The open wall structure adapted with recesses and ridges prevents the injection molded flat bottom structure to twist during solidification of the heated polymer. The bottom structure may have suitable size for the intended use. In particular thickness of 12 mm or less, 10 mm or less, 8 mm or less, 6 mm or less, 4 mm or less. The bottom structure may also embed well structures. The temperature transfer from the external heated surface to the specimens is thus optimized for the individual container, as well as ease of procedure is optimized when several various containers using same principle are used during an IVF procedure.

A third benefit being that the lid may be fitted to cover the area constraint by the innermost wall structure, while allowing the identification area to not be covered by the lid for easy identification.

The lid has protrusions on the upper side contacting recesses and ridges on the open wall structure during stacking of the containers on top of each other. This reduces risk of scratching the bottom, which can lead to reduced visibility of the specimens. This feature also ensures that only a container with its lid is gripped when reaching out towards the stacked products.

The lid having protrusions on the lower side ensuring that gas exchange can take place between the content of the container and the outside of the container with lid, e.g. during placement in gas controlled incubator.

The polymer container of the present invention is formed from a heated polymer, in particular a thermoplastic compound. Non-limiting examples of thermoplastic compounds that may be used are acrylonitrile butadiene styrene (ABS), acrylic, celluloid, cellulose acetate, Ethylene-Vinyl Acetate (EVA), Ethylene vinyl alcohol (EVAL), Flouroplastics, Liquid Crystal polymer (LCP), polyacetal, polyacrylate, polyacrylonitrile, polyamide, polyamide-omide (PAI polychlorotrifluoroethylene (PCTFE), polyethylene terephthalate (PET), polycyclohexylene dimethylene terephthalate (PCT), polycarbonate (PC), polyhydroxyalkanoates (PHAs), polyketone (PK), polyester, polyethylene (PE), polyetherketone (PEEK), polyetherimide (PEI), polyesthersulfone (PES), polyethylenechlorinates (PEC), polyimide (PI), polylactic acid (PLA), polymethylpentene (PMP), polyphenylene oxide (PPO), polyphenylene sulfide (PPS), polyphthalamide (PPA), polypropulene (PP), polystyrene (PS), polysulfone (PSU), polyurethane (PU), polyvinyl acetate (PVA), polyvinyl chloride (PVC), polyvinylidenechloride (PVDC) and styrene-acrylonitrile (SAM), or mixes or copolymers thereof.

In a particularly preferred embodiment the polymer container is formed from a polymeric material which is biocompatible.

The polymeric material may be selected such that it has a primarily hydrophobic or primarily hydrophilic surface or primarily in-between. In a particular embodiment the surface of the polymer article may be modified to make it in-between, e.g. by coating or by use of corona or plasma treatment. The polymers are generally hydrophobic by nature and the strength and time of the coating process determines the degree of hydrophilicity obtained.

Process for Producing a Polymer Container Optionally Functionalized by Surface Modification Typical methods used in the mass production of polymer articles are injection molding. Injection molding is performed by heating a suitable polymer until molten, injecting the molten polymer into a mold, allowing the polymer to cool and harden, and removing the molded article from the mold after solidification.

The surface of the polymer container is optionally made more hydrophilic to facilitate the formation of drops of media for culturing embryos, as well as made sterile to prevent contamination. Typically the surface of the polymer container is modified by corona or plasma treatment to increase surface wettability through electric discharge.

Sterilisation by irradiation (beta or gamma), steam autoclave, ethylene oxide, chemical disinfectants or dry heat are the typical sterilization methods used.

The sterile polymer container may further be functionalized by structuring the surface during the actual injection molding step and/or simply by wet chemical coating or vapor coating following the injection molding.

A functionalisation by adding structure to the surface of the polymer container during molding may be in the form of molded nano or micro structures within the polymer or by integrating a porous scaffold into the surface of the polymer container during injection molding. The structures allows specimens in contact with the structures within the container to obtain more 3D like morphology as well as intercommunicate with other specimens through the medium travelling unhindered through the structures retaining the specimens.

Coating using wet chemical process covalently bonds biological molecules to the polymer surface to facilitate specific functionality in relation to interaction with the surroundings being it meiose activation, cell attachment, molecule capture or separation and/or purification processes.

Coating using vapor process deposits oxide layers onto the surface of the polymer container. Examples of oxide layers may be $Al_2O_3$, $SiO_2$, $TiO_2$, $ZrO_2$, $CeO_2$ or a mixture or a multilayer structure thereof. Oxide layers may be deposited by Chemical Vapor deposition (CVD) or preferably by Molecular vapor deposition (MVD).

Experimental Example

The following examples serve to more fully describe the functionality of the externally flat bottom in contact with external heated surface compared to traditional containers for IVF. These examples do not limit the scope of the disclosure, but rather are presented for illustrative purposes.

Example 1

Temperature Transfer to Polymer Container

Two conventionally polymer containers with wells and a polymer container according to this invention are placed on a metal plate heated to 37.2 Degrees Celsius.

Figure 10:
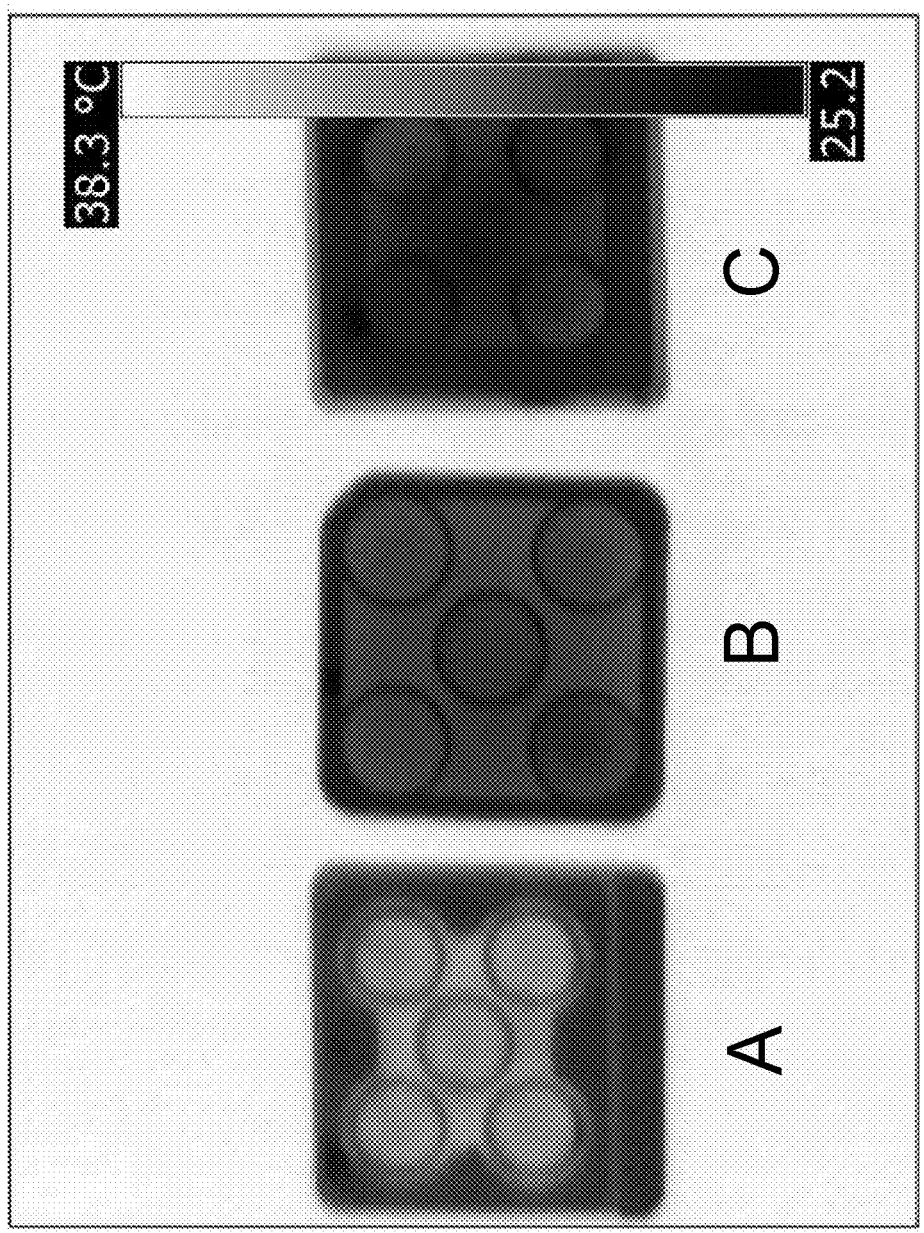
FIG. 10 shows a top view of an exemplary container in accordance with embodiments of this invention alongside two commercially available containers, all placed on an external surface heated to 37 degrees Celsius, illustrating temperature transfer and homogeneity in the different containers.

In FIG. 10 the two conventional polymer containers (B and C) have a bottom situated approx 0.5 mm above the heated plate surface. The container (A) according to this invention has full contact between the bottom of the container and the heated plate.

Each well is filled with liquid to obtain equal liquid height.

Allow 5 minutes for the heated plate to transfer heat to the containers.

Use a thermo sensitive camera to take an image of the heat distribution within the containers.

FIG. 10 illustrates the more optimal heat transfer from the heated plate to the liquid within the 5 well container (A) according to this example and this invention compared to commercially available 5 well (B) and 4 well (C) plates.

One conventionally polymer Petri dish and a polymer container according to this invention are placed on a metal plate heated to 37.2 Degrees Celsius.

Figure 11:
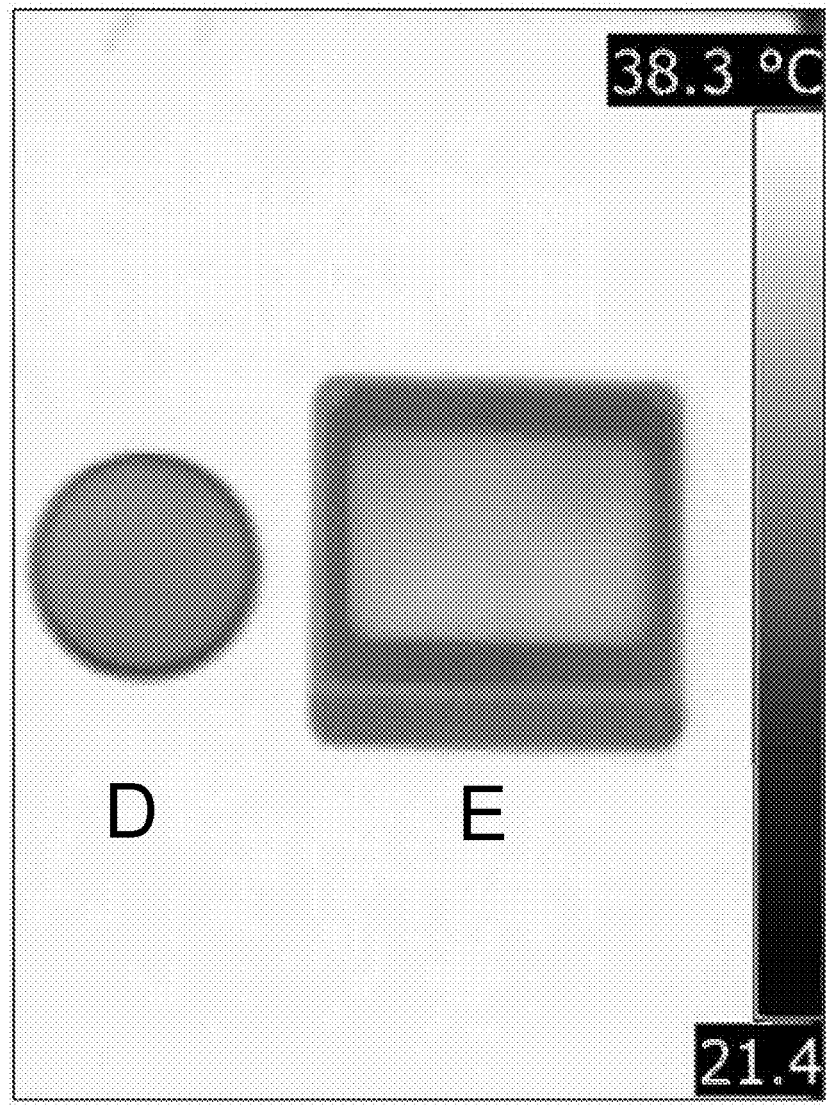
FIG. 11 shows a top view of a commercially available Petri dish alongside an exemplary container in accordance with embodiments of this invention, both placed on an external surface heated to 37 degrees Celsius, illustrating temperature transfer and homogeneity in the different containers.

In FIG. 11 the one conventional Petri dish (D) has a bottom situated approx 0.5 mm above the heated plate surface. The container (E) according to this invention has full contact between the bottom of the container and the heated plate.

Each container is filled with liquid to obtain equal liquid height.

Allow 5 minutes for the heated plate to transfer heat to the containers.

Use a thermo sensitive camera to take an image of the heat distribution within the containers.

FIG. 11 illustrates the more optimal heat transfer from the heated plate to the liquid within the container (E) according to this example and this invention compared to commercially available Petri dish (D).

Clearly, the polymer specimen of the invention has an improved ability of transferring heat to the liquid therein contained. In particular, the polymer specimen of the invention transports heat better than commercially available containers. The polymer specimen structure comprising ridges and recesses allows for a better contact between the heated plate and the bottom of the polymer specimen.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The following numbered items provide in term of conceptual statements further disclosure of the present subject matter.

1. A polymer specimen container comprising:
a specimen carrier, said carrier comprising a bottom base externally flat connected to a wall, said wall comprising an open hollow structure adapted to avoid twisting of said bottom base during the polymer specimen container production process.

2. A polymer specimen carrier according to item 1, wherein said open hollow structure comprises recesses and ridges adapted to provide stable support to said specimen carrier.

3. A polymer specimen carrier according to any of the preceding items wherein said open wall structure has its lowest level above the lowest level of said bottom base externally flat.

4. A polymer specimen container according to any of the preceding items further comprising a lid, said lid comprising a top and a bottom surface, wherein said top surface comprises protrusions complementary to at least one of said recesses or ridges in said open hollow wall structure.

5. A polymer specimen carrier according to any of the preceding items wherein said open hollow structure comprises area for identification means.

6. A polymer specimen carrier according to any of the preceding items, wherein said identification means is in the form of barcode, inscription, embossed text, writing or RFID tag.

7. A polymer specimen carrier according to any of the preceding items, wherein at least part of the internal surface of said bottom base externally flat is treated so as to modify its surface properties.

8. A polymer specimen carrier according to any of the preceding items, wherein said open wall structure forms substantially a square with or without rounded corners or being substantially circular.

9. A polymer specimen carrier according to any of the preceding items, wherein said open wall structure having an innermost wall structure forming a well substantially square with or without rounded corners, or being substantially circular.

10. A polymer specimen carrier according to any of the preceding items, wherein said innermost wall structure forms a circular well, wherein the centre of said circular well is substantially identical to the centre of the said specimen carrier.

11. A polymer specimen carrier according to any of the preceding items, wherein said flat bottom base externally flat comprises one or more individually separated wells for holding liquid medium sustaining the specimens during procedure.

12. A polymer specimen carrier according to item 11, wherein the internal surface of the bottom base of said individually separated wells has an inclination.

13. A polymer specimen carrier according to any of the preceding items comprising at least an innermost and an outermost wall structure, said innermost wall structure interconnected by a sterile bottom base being externally flat and having equal or lower base height than any other carrier structures, optimizing bottom base contact to a heated working surface and thereby improving heat transfer to the inside of the carrier.

14. A polymer specimen carrier according to any of the preceding items wherein the specimens are oocytes, embryos, blastocysts, spermatozoa or stem cells.

15. The use of a polymer specimen container according to any of the preceding items within the area of Assisted Reproductive Technology.

16. A method for producing a polymer specimen container according to items 2-15 wherein the presence of an open hollow structure comprising recesses and ridges prevents distortion of said flat bottom base during said polymer specimen carrier solidification.

What is claimed is:

1. A polymer specimen container comprising:
   a specimen carrier comprising a bottom base connected to a wall, said wall comprising an open hollow wall structure having reinforcements, said reinforcements being recesses and ridges configured to provide stable support to the specimen carrier, said bottom base being externally flat and configured to fully contact a heated plate,
   a lid configured to fit on the specimen carrier, the lid comprising a top and a bottom surface,
   wherein said top surface of said lid of the polymer specimen container comprises protrusions positioned to be complementary to at least one recess or ridge of an open hollow wall structure of an additional polymer specimen container when said additional polymer specimen container is stacked on top of said lid, thereby avoiding scratching of a bottom base of said additional polymer specimen container during stacking of said additional polymer specimen container on top of the polymer specimen container;
   wherein said open hollow wall structure of said specimen carrier comprises an innermost wall and an outermost wall,
   wherein said open hollow wall structure of said specimen carrier comprises a non-closed wall persisting in more than one plane,
   wherein said outermost wall of said open hollow wall structure of said specimen carrier has a lowest level above a lowest level of said bottom base, and
   wherein said recesses and ridges of said specimen carrier are positioned between said innermost wall and said outermost wall and above the lowest level of said bottom base of said specimen carrier, wherein at least one of said recesses and ridges of said specimen carrier is positioned to be complementary to a protrusion of a second lid of said additional polymer specimen container when said additional polymer specimen container is stacked below the specimen carrier to space the bottom base of said specimen carrier above said second lid of said additional polymer specimen container to avoid scratching of the bottom base of said specimen carrier when stacked;
   wherein said bottom base of said specimen carrier comprises a plurality of individually separated wells configured to hold liquid medium sustaining specimens during In Vitro Fertilization (IVF) procedures, wherein the plurality of individually separated wells are separated by walls configured to contain the liquid medium within each well, wherein the bottom base is externally flat and configured to fully contact the heated plate to provide temperature transfer to the liquid medium in the plurality of individually separated wells, and
   wherein said specimen carrier is configured to hold spermatozoa, sperm precursor cells, oocytes, pre-implantation embryos, zygotes, blastocysts, embryonic cells or stem cells during IVF procedures at 37 degrees Celsius when positioned on a heated surface.

2. The polymer specimen container according to claim 1, wherein said open hollow wall structure of said specimen carrier comprises an area for identification.

3. The polymer specimen container according to claim 2, wherein said area for identification comprises a barcode, inscription, embossed text, writing or RFID tag.

4. The polymer specimen container according to claim 1, wherein at least part of an internal surface of said bottom base of said specimen carrier that is externally flat is treated so as to modify its surface properties.

5. The polymer specimen container according to claim 1, wherein said open hollow wall structure of said specimen carrier forms a square with or without rounded corners or being circular.

6. The polymer specimen container according to claim 1, wherein said plurality of individually separated wells have a slope between a flat bottom of said plurality of individually separated wells and a well structure said walls separating said plurality of individually separated wells, and wherein said slope has an angle of 45 degrees or less.

7. The polymer specimen container according to claim 1, wherein said innermost wall structure and said outermost wall structure of said specimen carrier being interconnected by a bridging wall.

8. A method of using the polymer specimen container according to claim 1, in an assisted reproductive procedure comprising:
   providing the polymer specimen container of claim 1; and
   contacting said polymer specimen container with spermatozoa, sperm precursor cells, oocytes, pre-implantation embryos, zygotes, blastocysts, embryonic cells or stem cells during an assisted reproductive procedure.

9. The polymer specimen container according to claim 1, wherein a rim of said lid fits onto said open hollow wall structure of said polymer specimen carrier.

10. The polymer specimen container according to claim 1, wherein said lid further comprises small protrusions for securing gas exchange between an outer surface of said polymer specimen container and an internal surface of said polymer specimen container during use.

11. The polymer specimen container according to claim 1, said polymer specimen carrier being square or square with rounded corners having a side length of 25 mm or less.

12. The polymer specimen container according to claim 11, wherein said plurality of individually separated wells are circular in shape and having a diameter of 90 mm or less.

13. The polymer specimen container according to claim 1, wherein said polymer specimen carrier is circular and comprises a diameter of 120 mm or less.

14. The polymer specimen container according to claim 1 wherein said polymer specimen carrier comprises a height of 20 mm or less.

15. The polymer specimen container according to claim 1, wherein said bottom base that is externally flat of said specimen carrier comprises a thickness of 12 mm or less.

16. The polymer specimen container according to claim 1, wherein the bottom base of said specimen carrier is configured to fully contact the heated plate to provide homogeneous temperature transfer to the liquid medium in the plurality of individually separated wells.

17. The polymer specimen container according to claim 1, wherein the bottom base of said specimen carrier of said polymer specimen carrier is configured to be placed on an XY-stage station.

18. The polymer specimen container according to claim 1, wherein the bottom base of said specimen carrier has a base level lower than any other structure of the polymer specimen carrier.

19. The polymer specimen container according to claim 1, wherein said walls separating the plurality of individually separated wells protrude from an inner surface of the flat bottom base of said specimen carrier.

* * * * *